(12) United States Patent
Ogawa

(10) Patent No.: US 9,782,149 B2
(45) Date of Patent: Oct. 10, 2017

(54) ENDOSCOPE

(71) Applicant: OLYMPUS CORPORATION, Tokyo (JP)

(72) Inventor: Tomoaki Ogawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/705,532

(22) Filed: May 6, 2015

(65) Prior Publication Data

US 2015/0305711 A1    Oct. 29, 2015

Related U.S. Application Data

(63) Continuation of application No. PCT/JP2014/063393, filed on May 20, 2014.

(30) Foreign Application Priority Data

May 31, 2013   (JP) .................................. 2013-115371

(51) Int. Cl.
*A61B 8/00*  (2006.01)
*A61B 1/005*  (2006.01)
(Continued)

(52) U.S. Cl.
CPC .............. *A61B 8/445* (2013.01); *A61B 1/005* (2013.01); *A61B 1/0008* (2013.01); *A61B 1/018* (2013.01);
(Continued)

(58) Field of Classification Search
CPC ....... A61B 1/0008; A61B 1/005; A61B 1/018; A61B 1/05; A61B 8/12; A61B 8/445; A61B 8/4494
See application file for complete search history.

(56) References Cited

U.S. PATENT DOCUMENTS 6,224,555 B1   5/2001  Ouchi
2006/0173241 A1  8/2006  Ouchi et al.
(Continued)

FOREIGN PATENT DOCUMENTS

EP   0 066 185 A1   12/1982
EP   2641542 A1    9/2013
(Continued)

OTHER PUBLICATIONS

International Search Report dated Aug. 26, 2014 issued in PCT/JP2014/063393.

(Continued)

*Primary Examiner* — Mark Remaly
(74) *Attorney, Agent, or Firm* — Scully, Scott, Murphy & Presser, P.C.

(57) ABSTRACT

A first convex portion is arranged at an outer peripheral portion of a first support portion constituting a distal end portion of an insertion portion, and a protruding amount of the first convex portion is set such that an outer peripheral length of the distal end portion including the first convex portion is smaller than an outer peripheral length determined based on a distal end outer diameter as an effective outer diameter of the distal end portion, to thereby ensure durability without an unnecessary increase in a size of the distal end portion and improve insertability of the distal end portion into a subject.

7 Claims, 7 Drawing Sheets

(51) Int. Cl.
*A61B 1/00* (2006.01)
*A61B 1/018* (2006.01)
*A61B 1/05* (2006.01)
*A61B 8/12* (2006.01)

(52) U.S. Cl.
CPC .................. *A61B 1/05* (2013.01); *A61B 8/12* (2013.01); *A61B 8/4494* (2013.01)

(56) References Cited

U.S. PATENT DOCUMENTS

| | | |
|---|---|---|
| 2010/0179434 A1 | 7/2010 | Thornton |
| 2011/0301413 A1 | 12/2011 | Morimoto |
| 2013/0158410 A1 | 6/2013 | Ohgishi et al. |

FOREIGN PATENT DOCUMENTS

| | | |
|---|---|---|
| JP | H01-285250 A | 11/1989 |
| JP | H11-347037 A | 12/1999 |
| JP | 2001-204731 A | 7/2001 |
| JP | 2006-192091 A | 7/2006 |
| JP | 2011-206428 A | 10/2011 |
| JP | 5253691 B1 | 7/2013 |
| WO | WO 2013/035374 A1 | 3/2013 |

OTHER PUBLICATIONS

Extended Supplementary European Search Report dated Nov. 25, 2016 in related European Patent Application No. 14 80 4044.7.

ENDOSCOPE

CROSS REFERENCE TO RELATED APPLICATION

This application is a continuation application of PCT/JP2014/063393 filed on May 20, 2014 and claims benefit of Japanese Application No. 2013-115371 filed in Japan on May 31, 2013, the entire contents of which are incorporated herein by this reference.

BACKGROUND OF THE INVENTION

1. Field of the Invention

The present invention relates to an endoscope which incorporates at a distal end portion thereof an observation portion such as an ultrasound observation portion.

2. Description of the Related Art

Generally, endoscopes have a rigid distal end portion at a distal end of an elongated insertion portion to be inserted into a subject or the like. Such distal end portion includes various observation portions such as an ultrasound observation portion that transmits and receives ultrasound and an optical observation portion that picks up an optical image, and the observation portions are housed in a case made of a rigid member such as metal or resin. The shape of the rigid member configuring the case or the like roughly defines the outer shape of the distal end portion of the endoscope.

Generally, corner portions at which two or more planes or curved faces and the like are aggregated exist at the distal end side of the case. For example, as illustrated in Japanese Patent Application Laid-Open Publication No. 2011-206428, in the convex-type ultrasound endoscope, the case (first support portion) configuring the distal end portion includes side faces located respectively on both sides of the acoustic lens portion of the ultrasound transducer, a face (bottom face) opposed to the rear face side of the acoustic lens portion, and end face which is continuously formed at the distal end side of these side faces and the bottom face, and corner portions are formed respectively at the aggregation portions of these faces.

Among the corner portions formed in the case, the corner portions formed between the end face and other faces are likely to interfere with the body wall or the like and to be an insertion resistance when inserting the endoscope into the narrow bronchus and the like. Therefore, in order to reduce such an insertion resistance, the corner portions of the case configuring the distal end portion are generally subjected to a predetermined rounding processing and the like.

SUMMARY OF THE INVENTION

An endoscope according to one aspect of the present invention includes: an insertion portion to be inserted into a subject; a distal end portion arranged at a distal side with respect to the insertion portion and including an observation portion having a convex observation face that transmits and receives ultrasound and a first support portion configured to be able to house the observation portion; and a convex portion formed integrally with at least a side face of the first support portion, the side face intersecting with a face on which the observation face is arranged, wherein an outer peripheral length of a part of the distal end portion, the part including the convex portion, is smaller than an outer peripheral length at a part located on a more proximal end side than the convex portion.

DETAILED DESCRIPTION OF THE PREFERRED EMBODIMENTS

Figure 1:
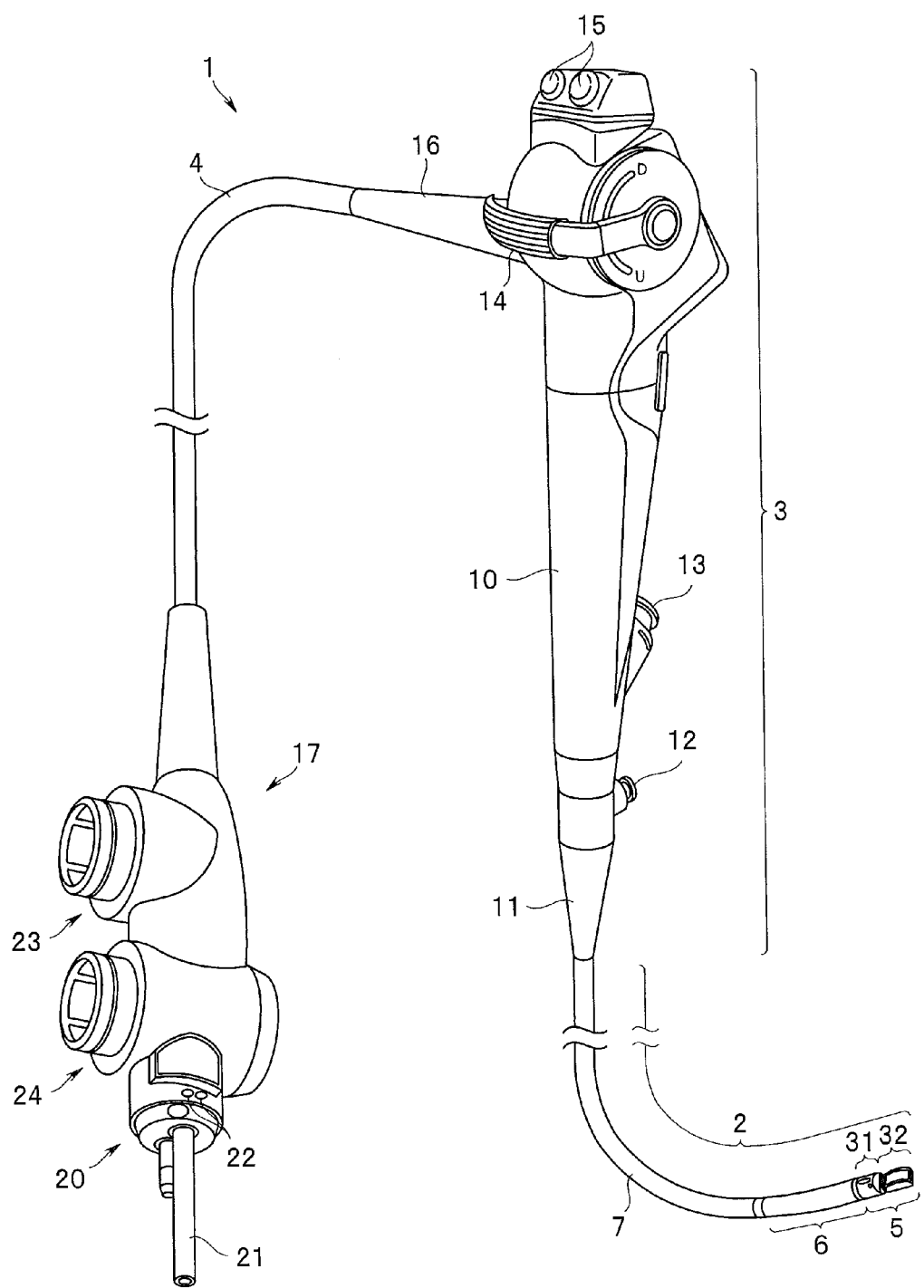
FIG. 1 relates to a first embodiment of the present invention and is a general view of an endoscope.
Figure 2:
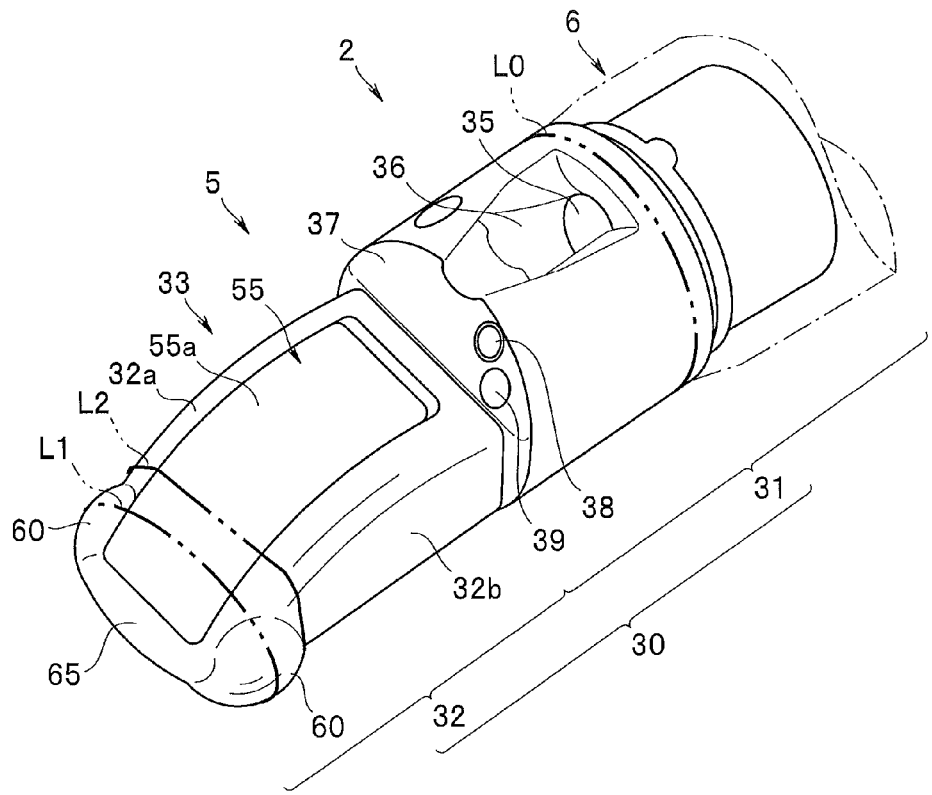
FIG. 2 relates to the first embodiment and is a perspective view of a distal end portion viewed from a diagonally upper direction.
Figure 3:
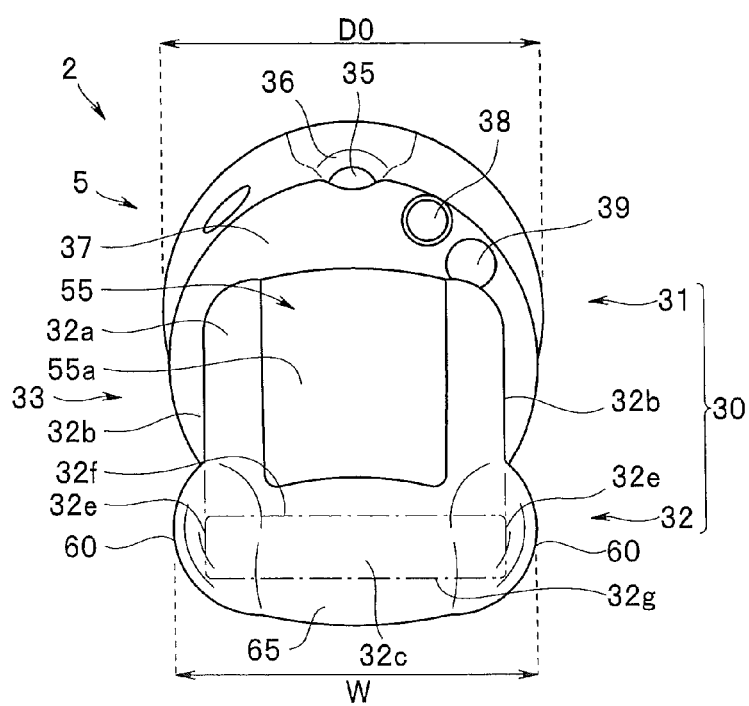
FIG. 3 relates to the first embodiment and is a view of an end face of the distal end portion.
Figure 4:
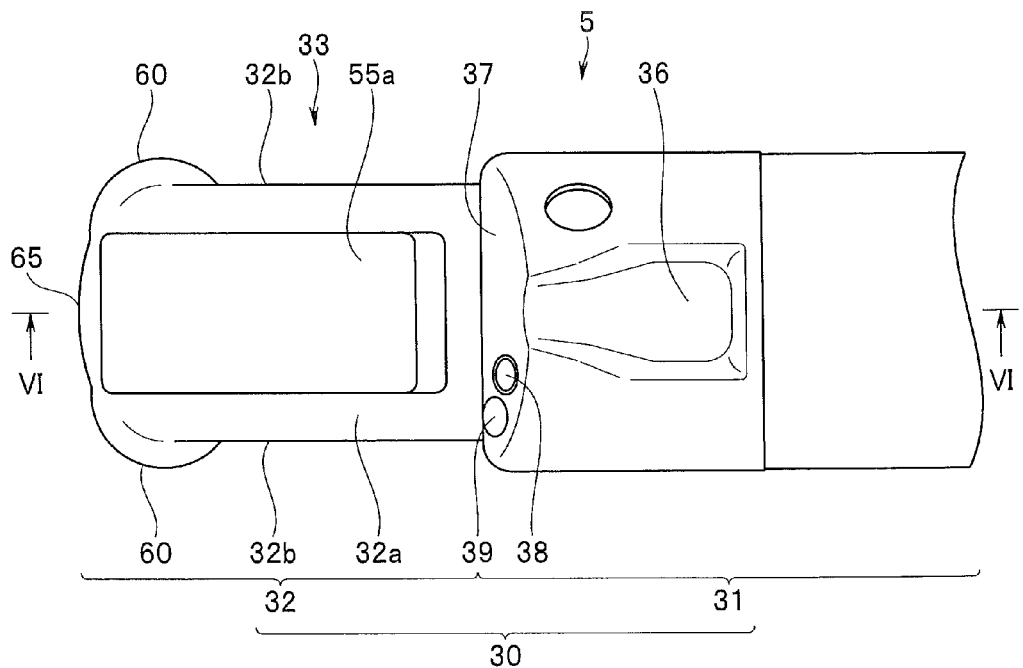
FIG. 4 relates to the first embodiment and is a top view of the distal end portion.
Figure 5:
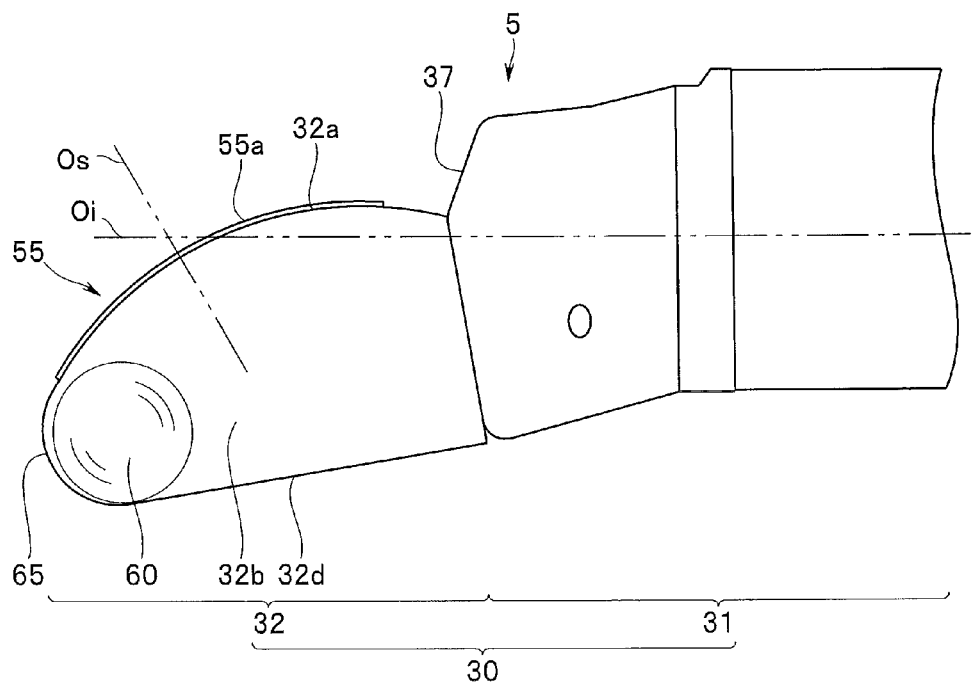
FIG. 5 relates to the first embodiment and is a left side view of the distal end portion.
Figure 6:
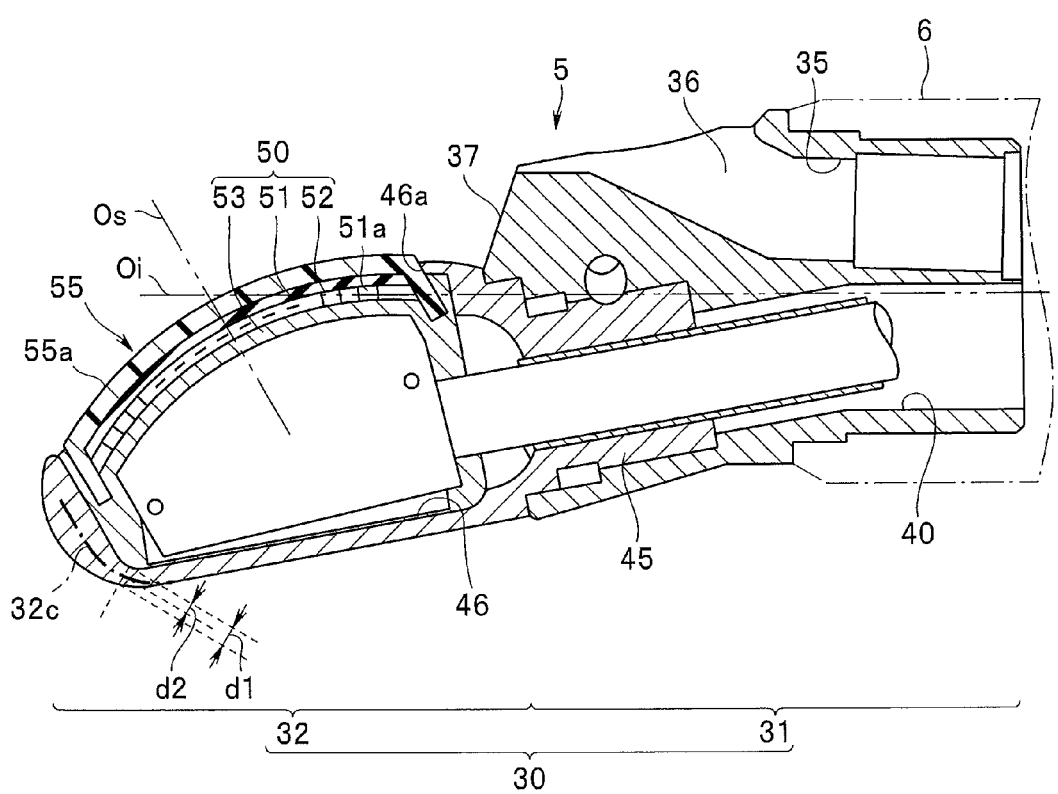
FIG. 6 relates to the first embodiment and is a cross-sectional view taken along the VI-VI line in FIG. 4.
Figure 7:
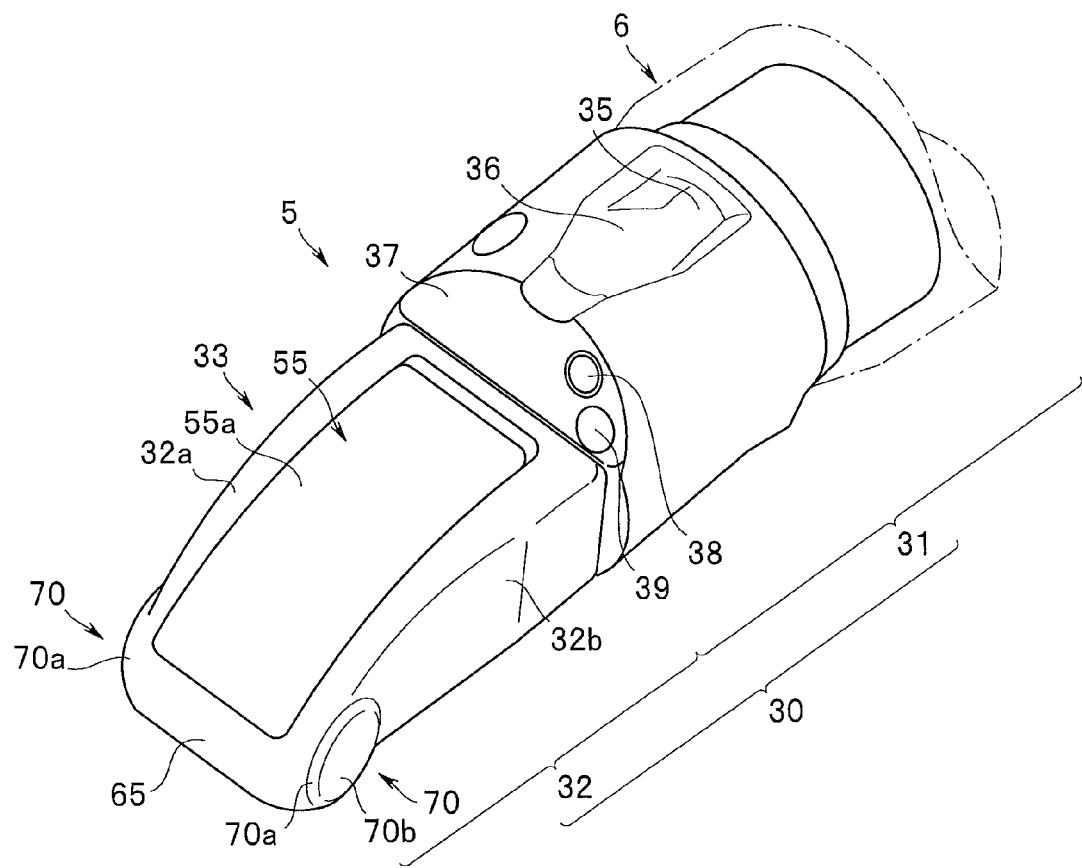
FIG. 7 relates to a modified example of the first embodiment and is a perspective view of the distal end portion.

Hereinafter, embodiments of the present invention will be described with reference to drawings. FIGS. 1 to 6 relate to the first embodiment of the present invention in which: FIG. 1 is a general view of an endoscope; FIG. 2 is a perspective view of a distal end portion viewed from a diagonally upper direction; FIG. 3 is a view of an end face of the distal end portion; FIG. 4 is a top view of the distal end portion; FIG. 5 is a left side view of the distal end portion; and FIG. 6 is a cross-sectional view taken along the VI-VI line in FIG. 4.

An endoscope 1 shown in FIG. 1 is an endoscope for bronchus (bronchoscope), for example, and more specifically, the endoscope 1 is an ultrasound bronchoscope provided with an ultrasound observation portion for obtaining an ultrasound image and an optical observation portion for obtaining an optical image in the present embodiment. The endoscope 1 includes: an elongated insertion portion 2 which is insertable into a site to be observed such as the bronchus in a subject; an operation portion 3 provided in a linked manner on the proximal end side of the insertion portion 2; and a universal cord 4 extended from the side portion of the operation portion 3.

Furthermore, the insertion portion 2 includes at the distal end thereof the following components in a linked manner in the following order from the distal end: a distal end portion 5; a bendable bending portion 6 disposed on the proximal end side of the distal end portion 5; and a long flexible tube portion 7 having flexibility and disposed on the proximal end side of the bending portion 6.

The operation portion 3 includes an operation portion main body 10 which configures an operation grasping portion, and the distal end side of the operation portion main body 10 is connected to the proximal end side of the flexible tube portion 7 through a break prevention portion 11. In addition, the operation portion main body 10 includes, at positions closer to the distal end thereof, an air/water feeding port 12 which is an opening portion of an air/water feeding channel (not shown) as a conduit located inside the insertion portion 2, and a treatment instrument insertion port 13 which is an opening portion on the proximal end side of a treatment instrument insertion channel (not shown) as a conduit through which a treatment instrument is inserted into the insertion portion 2. On the other hand, the operation portion main body 10 includes at positions closer to the proximal end thereof, an angle lever 14 for performing bending operation of the bending portion 6 and various endoscope function switches 15.

One end side of the universal cord 4 is connected to the side portion of the operation portion main body 10 through a break prevention portion 16. On the other hand, at the extension end which is the other end side of the universal cord 4, a scope connector portion 17 is provided. At the end portion of this scope connector portion 17, a light source side connector 20, which is attachable to and detachable from a light source apparatus, not shown, is provided. The proximal end portion of a light guide 21 extended from the insertion portion 2 is protruded from the light source side connector 20 and an electric contact 22 is disposed on the light source side connector 20. Connection of the light source side connector 20 to the light source apparatus allows the light guide 21 to be optically connected to a light source in the light source apparatus, and allows the electric contact 22 to be electrically connected to the power source in the light source apparatus. In addition, the scope connector portion 17 includes at the side portion thereof an ultrasound connector 23 which is attachable to and detachable from an ultrasound observation apparatus, not shown, and an electrical connector 24 which is attachable to and detachable from a video processor, not shown.

Next, description will be made on the specific configuration of the distal end portion 5 of the endoscope 1, with reference to FIGS. 2 to 6. As shown in FIG. 6, the distal end portion 5 includes a distal end rigid member 30 as a rigid frame body, for example. The distal end rigid member 30 according to the present embodiment includes a second support portion 31, the base portion side of which is connected to the bending portion 6, and a first support portion 32 that protrudes from the distal end side of the second support portion 31.

The second support portion 31 is made of a rigid member, for example. The second support portion 31 includes inside thereof a channel communication hole 35 pierced so as to communicate with the treatment instrument insertion channel, and the opening formed on the peripheral face of the second support portion 31 by the channel communication hole 35 is set as a suction/forceps port 36.

In addition, the second support portion 31 includes, at the distal end thereof, an inclined face 37 formed so as to be inclined at a predetermined angle with respect to an insertion axis Oi of the insertion portion 2 at a position which is in the vicinity of the suction/forceps port 36 and is offset from the insertion axis Oi to one side. On the inclined face 37, an objective lens 38 and an illumination lens 39 which configure the optical observation portion as the observation portion are disposed (see FIGS. 2 to 4). However, both the channel communication hole 35 and the objective lens 38 do not have to be arranged, and only one of them may be arranged.

In addition, the second support portion 31 includes a cable insertion hole 40 pierced so as to communicate with the interior of the bending portion 6. In the cable insertion hole 40, a fitting shaft portion 45 protruded from the base portion of the first support portion 32 is fitted. The fitting shaft portion 45 is fixed with a screw or the like, to thereby allow the first support portion 32 to be held by the second support portion 31.

The first support portion 32 according to the present embodiment is configured by a metal member, the basic form of which is a box shape which can house an ultrasound transmission and reception portion 50, for example. As exemplified in FIG. 5, among the faces which constitute the outer peripheral face of the first support portion 32, the face which is continuous with the inclined face 37 of the second support portion 31 is set as a contact face 32a which is brought into contact with the site to be observed of the subject at the time of ultrasound observation. The contact face 32a is configured by a bending face bent in a substantially arc shape with respect to the direction of the insertion axis Oi, for example.

In addition, the contact face 32a includes a substantially rectangular-shaped opening portion 46a which allows a housing chamber 46 formed inside the first support portion 32 to communicate with outside. The ultrasound transmission and reception portion 50 is housed in the first support portion 32 through the opening portion 46a.

The ultrasound transmission and reception portion 50 according to the present embodiment configures, together with an acoustic lens portion 55, for example, a convex-type ultrasound observation portion 33 at the distal end portion 5.

The acoustic lens portion 55 is made of a silicone resin or the like, for example, and converges the ultrasound beams transmitted from the ultrasound transmission and reception portion 50. The outer face of the acoustic lens portion 55 is set so as to be substantially flush with the contact face 32a of the first support portion 32 with respect to the direction of the insertion axis Oi, and is configured by a bending face bent in a substantially arc shape with respect to the direction of the insertion axis Oi. The outer face of the acoustic lens portion 55 thus configured forms an observation face 55a of the ultrasound transmission and reception portion 50.

The ultrasound transmission and reception portion 50 includes an ultrasound transducer 51, an acoustic matching layer 52, and a backing member 53.

The ultrasound transducer 51 is configured by an alignment of a plurality of piezoelectric elements 51a made of piezoelectric ceramics, for example. In the present embodiment, the respective piezoelectric elements 51a are aligned on the inner face side of the acoustic lens portion 55 such that the alignment of the piezoelectric elements forms substantially an arc shape with respect to the direction of the insertion axis Oi, and the piezoelectric elements convert electric signals into ultrasound signals and vice versa.

The acoustic matching layer 52 is configured by a substantially plate-shaped member interposed between the ultrasound transducer 51 and the acoustic lens portion 55. The acoustic matching layer 52 is provided for reducing the acoustic impedance between the ultrasound transducer 51 and the acoustic lens portion 55, and the acoustic matching layer 52 allows the ultrasound transmitted and received by the ultrasound transducer 51 to pass therethrough.

The backing member 53 is a member which absorbs the ultrasound emitted from the ultrasound transducer 51 to the inside of the housing chamber 46 and the ultrasound from the inside of the housing chamber 46 to the ultrasound transducer 51. In the present embodiment, the ultrasound transducer 51 transmits and receives ultrasound only in the normal line direction of the observation face 55a.

The first support portion 32, which houses the ultrasound transmission and reception portion 50 thus configured, includes first convex portions 60, as projection portions, provided respectively on the side faces 32b which intersect with the face (contact face 32a) on which the observation face 55a are arranged, as shown in FIGS. 2 to 5. More specifically, among the respective faces constituting the peripheral face of the first support portion 32, the side faces 32b, which are located respectively on the right and left of the observation face 55a with the direction of the insertion axis Oi as a reference, are provided with the first convex portions 60 protruded respectively in the directions of the right and left width of the observation face 55a.

In the present embodiment, each of the first convex portions 60 is configured by a substantially semispherical-shaped projection members formed integrally with the first support portion 32, for example. These first convex portions 60 are preferably arranged on the more distal end side than the intersection point at which the insertion axis Oi and the scanning central axis Os of the ultrasound observation portion 33 intersect. In the present embodiment, the first convex portions 60 are arranged at substantially distal-most positions of the respective side faces 32b.

In this case, the protruding amount of the first convex portions 60 is set such that the outer peripheral length (maximum outer peripheral length) L1 of the first support portion 32 at the part where the first convex portions 60 are formed is relatively smaller than the outer peripheral length (maximum outer peripheral length) L0 determined based on a distal end outer diameter D0 which is the effective outer diameter of the distal end portion 5 (see FIG. 1). In addition, it is preferable that the protruding amount of the respective convex portions 60 is set such that the outer peripheral length L1 of the first support portion 32 at the part where the first convex portions 60 are formed is relatively larger than the outer peripheral length L2 of the first support portion 32 at the part located on the more proximal end side than the first convex portions 60. Furthermore, it is preferable that the protruding amount of the first convex portions 60 is set such that the width (maximum width) W of the first support portion at the part where the first convex portions 60 are formed is equal to or smaller than the distal end outer diameter D0 of the distal end portion (see FIGS. 3 and 4).

In addition, the first support portion 32 includes at the distal end thereof a second convex portion 65 that protrudes in the direction of the insertion axis Oi. In the present embodiment, the second convex portion 65 is formed integrally with the first support portion 32, and configured by a curved-face-shaped projection member protruding from substantially the entire region of the end face 32c of the first support portion 32. Note that the above-described end face 32c is a design end face to be formed when supposing that a wall portion having a minimal thickness is provided at the distal end of the first support portion 32 in order to ensure the function as the first support portion 32 (see the one-dot chain line in FIG. 3, for example). The end face 32c does not actually exist in the present embodiment in which the second convex portion 65 is provided so as to protrude from substantially the entire region of the distal end of the first support portion 32.

It is preferable that the second convex portion 65 forms a curved face continuous with the first convex portions 60 located respectively on the right and left of the second convex portion 65. Therefore, the second convex portion 65 in the present embodiment is configured by a projection member having a substantially partial spheroidal shape, for example. In this case, as shown in FIG. 5, for example, the radius of curvature of the second convex portion 65 is preferably set to be relatively smaller than the radius of curvature of the contact face 32a.

According to such an embodiment, the first convex portions 60 each having a curved face are arranged at the outer peripheral portion of the first support portion 32 which constitutes the distal end portion 5 of the insertion portion 2, and the protruding amount of the first convex portions 60 is set such that the outer peripheral length L1 of the distal end portion 5 including the first convex portions 60 is smaller than the outer peripheral length L0 determined based on the distal end outer diameter D0 which is the effective outer diameter of the distal end portion 5, which enables the durability to be ensured and also enables the insertability of the distal end portion 5 into the subject to be improved, without an unnecessary increase in the size of the distal end portion 5.

That is, the first convex portions 60 are arranged on the outer peripheral portion of the first support portion 32, thereby enabling a predetermined region located more on the base portion side than the first convex portions 60 to be relatively thinner. As a result, it is possible to reduce the contacting area between the body wall, etc., and the outer peripheral face of the distal end portion 5. In this case, each of the first convex portions 60 has a curved face, which can reduce the insertion resistance due to the interference with the body wall at the time of inserting the distal end portion. Furthermore, the protruding amount of the first convex portions 60 is set such that the outer peripheral length L1 of the distal end portion 5 including the first convex portions 60 is smaller than the outer peripheral length L0 determined based on the distal end outer diameter D0, to thereby capable of preventing the first convex portions 60 from becoming a substantive resistance at the time of inserting the distal end portion into the subject. Therefore, such a configuration can improve the insertability of the insertion portion 2 into the subject.

In addition, since the first convex portions 60 are located at the distal-most of the side faces 32b, respectively, the first convex portions 60 can cover the corner portions 32e which are supposed to be formed on the distal end side of the first support portion 32 by the contact face 32a and side faces 32b intersecting with the end face 32c formed continuously with the contact face and side faces, on the right and left sides of the first support portion 32 (see FIG. 3). The corner portions 32e are thus covered with the first convex portions 60, thereby capable of eliminating the corner portions 32e which are supposed to be formed respectively on both right and left sides of the first support portion 32 at the distal end thereof. If the corner portions 32e which are assumed to cause an interference with the body wall, in particular, at the time of insertion are thus eliminated, there is no need for performing rounding processing on the corner portions. As a result, it is not necessary to increase the entire thickness of the respective wall portions of the first support portion 32 in accordance with the rounding processing or the like. Therefore, it is possible to sufficiently ensure the durability of the first support portion 32, while suppressing the unnecessary increase in the size of the distal end portion 5.

Furthermore, the second convex portion 65 protruding from substantially the entire region of the end face 32c of the first support portion 32 is provided in addition to the first convex portions 60, which can eliminate the corner portions 32f which are supposed to be formed between the contact face 32a and the end face 32c, and the corner portions 32g which are supposed to be formed between the rear face 32d which is the face opposed to the contact face 32a (observation face 55a) and the end face 32c (see FIG. 3). Therefore, even in such a case, there is no need for increasing the entire thickness of the respective wall portions of the first support portion 32 in accordance with the rounding processing, or the like. Therefore, it is possible to further improve the insertability and prevent the unnecessary increase in the size of the distal end portion 5 while sufficiently ensuring the durability of the first support portion 32.

In the case where the second convex portion 65 is provided as described above, the entire length of the first support portion 32 becomes larger. However, the radius of curvature of the second convex portion 65 is set to be relatively smaller than the radius of curvature of the contact face 32a, to thereby surely prevent the second convex portion 65 from being an actual blockade at the time of bending operation even when the direction of the contact face 32a is changed with respect to the body wall or the like by bending the bending portion 6, for example.

FIG. 6 shows one example of comparing the thickness in the case where the corner portions are covered with the convex portion and the thickness in the case where the corner portions are subjected to rounding processing. The example shown in FIG. 6 illustrates the respective thicknesses d1, d2 in the case where the corner portions 32g are covered with the second convex portion 65 and in the case where the corner portions 32g are subjected to the rounding processing. As is clear from FIG. 6, the thickness d1 can be sufficiently ensured, compared with the thickness d2. Though not shown, it is needless to say that also the relationship between the corner portions 32e and the first convex portions 60 and the relationship between the corner portions 32f and the second convex portion 65 are substantially the same as that described above.

In the above-described first embodiment, description was made on the one example in which the entire faces of the first and second convex portions are formed with curved faces. However, only predetermined partial regions of the first and second convex portions, which are supposed to be an interference with the body wall or the like, may be formed with curved faces.

For example, as shown in FIGS. 7 to 11 as a modified example of the first embodiment, first convex portions 70 each can be configured by a combination of an annular-shaped partial spherical portion 70a and a plane portion 70b formed continuously with the partial spherical portion 70a. If the first convex portions 70 are thus configured, the protruding amount of the first convex portions 70 can be reduced and insertability into a subject can be further improved.

Figure 8:
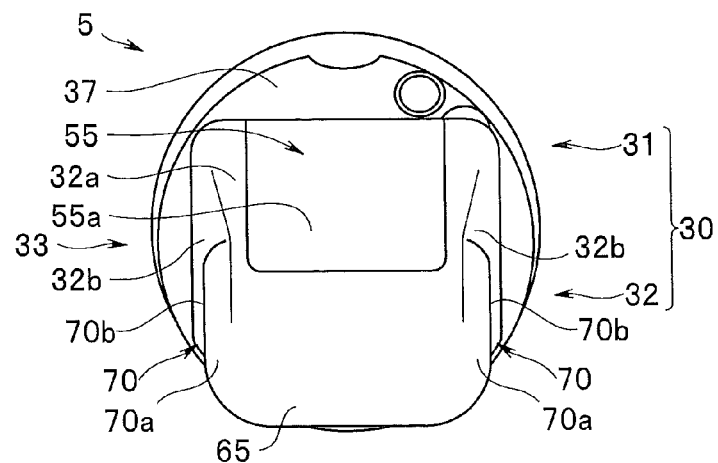
FIG. 8 relates to the modified example of the first embodiment and is a view of an end face of the distal end portion.
Figure 9:
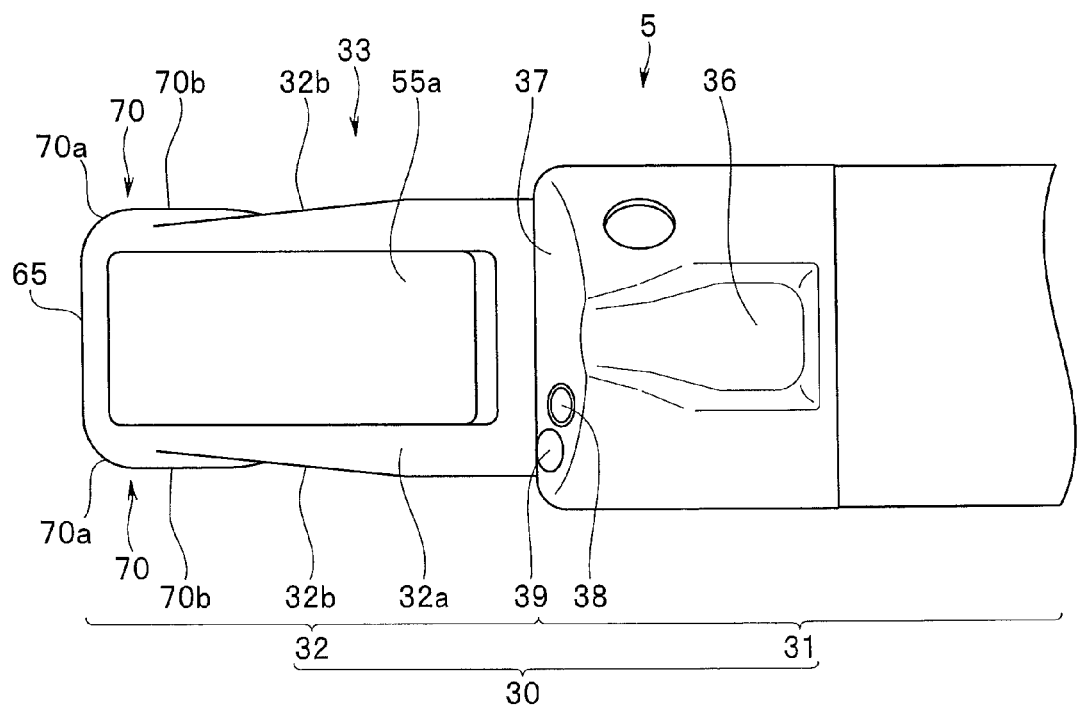
FIG. 9 relates to the modified example of the first embodiment and is a top view of the distal end portion.

The first support portion 32 shown in the present modified example has a tapered shape in which the width between the side faces 32b becomes narrower from the base portion side toward the distal end side, as shown in FIGS. 8, 9, for example. In such a shape, in order to obtain more preferred insertability, it is preferable that the width of the distal end side part where the first convex portions 70 are provided is set to be equal to or narrower than the width of the base portion side of the first support portion 32. In the present modified example, the positions of the plane portions 70b are changed, to thereby adjust the protruding amount of the first convex portions 70 without changing the radius of curvature, etc. of the partial spherical portion 70a.

Figure 10:
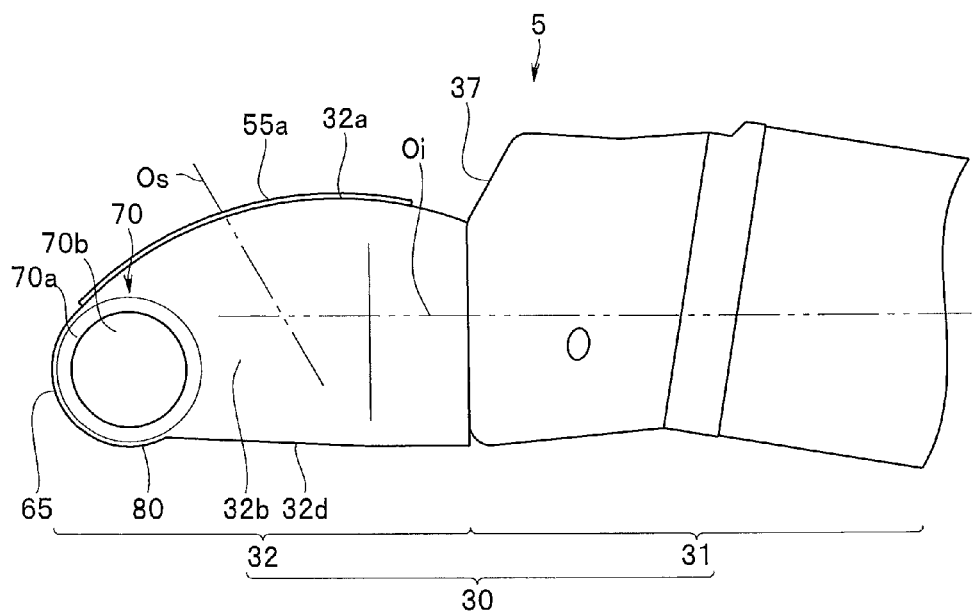
FIG. 10 relates to the modified example of the first embodiment and is a left side view of the distal end portion.
Figure 11:
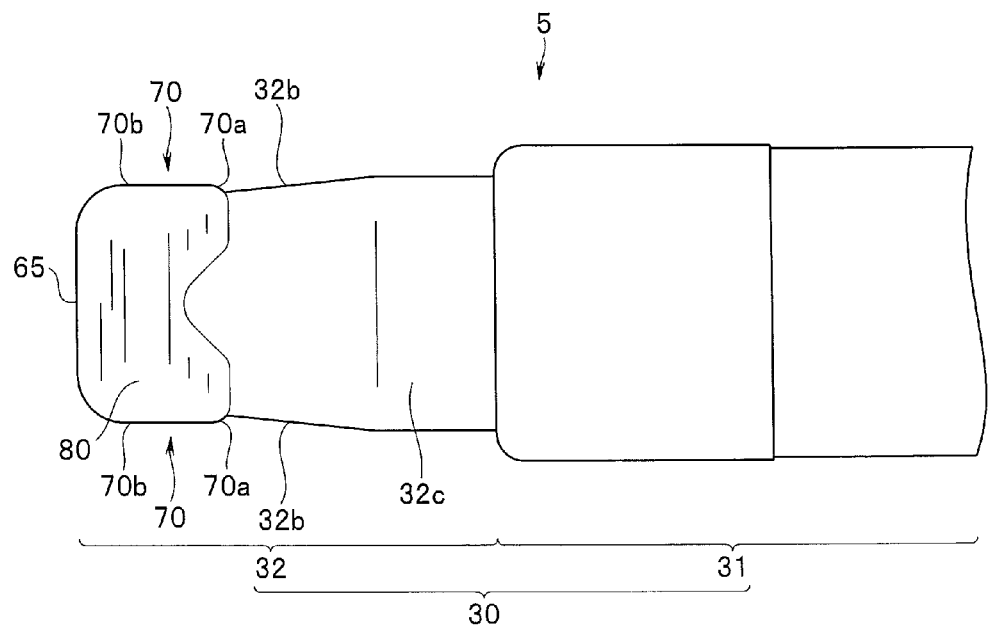
FIG. 11 relates to the modified example of the first embodiment and illustrates a bottom face of the distal end portion.

In addition, the first support portion 32 shown in the present modified example is provided with a third convex portion 80 as a projection portion also on the rear face 32d which is the face opposed to the contact face 32a (observation face 55a) among the respective faces constituting the outer peripheral face of the first support portion 32. It is preferable that the third convex portion 80 is configured with a curved face having a predetermined continuity with the first convex portions 70 provided respectively on the right and left sides of the third convex portion and the second convex portion 65 provided on the distal end side, as shown in FIGS. 10, 11, for example. Note that, it is needless to say that, even in the case where the third convex portion 80 is provided, the respective protruding amounts of the first and third convex portions 70, 80 should be set such that the outer peripheral length of the part where the first and third convex portions 70, 80 are provided becomes smaller than the outer peripheral length L0 determined based on the distal end outer diameter D0.

The present invention is not limited to the above-described embodiments, and various modifications and changes are possible, and such modifications and changes are also included in the technical range of the present invention. For example, it is needless to say that the configurations in the above-described embodiment or modified example may be appropriately combined. In addition, the present invention can be applied to a rigid endoscope including a rigid insertion portion which does not include a bending portion.

In the above-described embodiments, description has been made on the example in which the present invention is applied to a bronchoscope which is particularly required to have a reduced diameter. However, it is needless to say that the present invention is not limited to the example, and can be applied to endoscopes for digestive organs, circulatory organs, cerebral surgery, urinary organs and genitals, for example.

What is claimed is:
1. An endoscope comprising:
an insertion portion to be inserted into a subject;
a distal end portion arranged at a distal end of the insertion portion and including an ultrasound observation portion having a convex observation face that transmits and receives ultrasound and a first support portion configured to be able to house the ultrasound observation portion; and
a convex portion formed on at least one of first and second opposed side faces of the first support portion, the at least one of the first and second opposed side faces intersecting with a face on which the observation face is arranged,
wherein an outer peripheral length of a part of the distal end portion, the part including the convex portion, is smaller than an outer peripheral length at a part located on a more proximal end side than the convex portion; and
wherein the first support portion having a cavity defined by the first and second opposed side faces, a rear face and the convex observation face.
2. The endoscope according to claim 1, wherein the convex portion is arranged on a more distal end side than an intersection point at which an insertion axis of the insertion portion and a scanning central axis of the ultrasound observation portion intersect with each other.
3. The endoscope according to claim 1, wherein
the distal end portion includes a second support portion arranged at a proximal end side of the first support portion, the second support portion including a channel communication hole that communicates with a treatment instrument channel or a visible light observation portion that performs visible light observation, and
the outer peripheral length of the part of the distal end portion, the part including the convex portion, is smaller than an outer peripheral length of the second support portion.
4. The endoscope according to claim 1, wherein the outer peripheral length of the part including the convex portion is larger than an outer peripheral length of a part of the distal end portion, the part being adjacent to a proximal end side of the convex portion.

5. The endoscope according to claim 1, wherein the convex portion is formed on each of the first and second opposed side faces.

6. The endoscope according to claim 1, wherein the convex portion is further formed on the rear face, the rear face being opposed to the face on which the observation face is arranged.

7. The endoscope according to claim 1, wherein a width orthogonal to a longitudinal axis of the distal end portion at the convex portion is wider than a smallest width of the distal end portion at the convex observation portion.

* * * * *